(12) United States Patent
Nakamura et al.

(10) Patent No.: US 7,807,177 B2
(45) Date of Patent: Oct. 5, 2010

(54) SEGMENT OF GLYCOSYLATION-DEFICIENT HGFALPHA-CHAIN

(75) Inventors: Toshikazu Nakamura, 1-4, Hosojicho, Okazaki, Sakyo-ku, Kyoto 606-8333 (JP); Kunio Matsumoto, Mino (JP); Kazuhiro Fukuta, Mino (JP)

(73) Assignees: Toshikazu Nakamura, Kyoto (JP); Kringle Pharma Inc., Osaka (JP)

( * ) Notice: Subject to any disclaimer, the term of this patent is extended or adjusted under 35 U.S.C. 154(b) by 569 days.

(21) Appl. No.: 10/926,088

(22) Filed: Aug. 26, 2004

(65) Prior Publication Data

US 2005/0164918 A1   Jul. 28, 2005

(30) Foreign Application Priority Data

Jan. 27, 2004   (JP) .............................. 2004-018882

(51) Int. Cl.
*C07K 14/575* (2006.01)
*A61K 38/22* (2006.01)
*C12N 15/00* (2006.01)

(52) U.S. Cl. ..................... 424/198.1; 530/350; 435/440

(58) Field of Classification Search ........................ None
See application file for complete search history.

(56) References Cited

U.S. PATENT DOCUMENTS

2003/0162736 A1* 8/2003 Nakamura et al. ............ 514/44

OTHER PUBLICATIONS

Date et al. FEBS Letters 420: 1-6, Jan. 1998.*
Shimizu et al. Biochemical and Biophysical Research Communications 189(3): 1329-1335, Dec. 30, 1992.*
Glass and Heinz, Chapter 6, Artificial DNA Methods and Applications, Editors Khudyakov and Fields, CRC Press, London, (2003).*
Mizuno et al., The Journal of Biological Chemistry, 269(2): 1131-1136, Jan. 14, 1994.*
Bruce-Chwatt LJ. British Medical Journal, 285: 674-676. (1982).*
Fukuta et al. Biochem J. 388:555-562 (2005).*
N. Shimizu et al., "Hepatocyte Growth Factor is Linked by O-Glycosylated Oligosaccharide on the α Chain", Biochemical and Biophysical Research Communications, vol. 189, No. 3, pp. 1329-1335, Dec. 30, 1992.
S. J. Stahl et al., "Functional and Biophysical Characterization of Recombinant Human Hepatocyte Growth Factor Isoforms Produced in *Escherichia coli*", Biochem. J., vol. 326, pp. 763-772, 1997.
K. Kuba et al., "Kringle 1-4 of Hepatocyte Growth Factor Inhibits Proliferation and Migration of Human Microvascular Endothelial Cells", Biochemical and Biophysical Research Communications, vol. 279, No. 3, pp. 846-852, Dec. 29, 2000.
R. Hofmann et al., "Scatter factor is a glycoprotein but glycosylation is not required for its activity", Biochimica et Biophysica Acta, vol. 1120, No. 3, pp. 343-350, 1992.
N. Shimizu et al., "Hepatocyte Growth Factor is Linked by O-Glycosylated Oligosaccharide on the α Chain", Biochemical and Biophysical Research Communications, vol. 189, No. 3, pp. 1329-1335, Dec. 30, 1992.
K. Date et al., "HGF/NK4 is a specific antagonist for pleiotrophic actions of hepatocyte growth factor", FEBS Letters, vol. 420, No. 1, pp. 1-6, 1997.
K. Fukuta et al., "Multiple Biological Responses are Induced by Glycosylation-Deficient Hepatocyte Growth Factor", Biochemical Journal, Feb. 4, 2005.

* cited by examiner

*Primary Examiner*—Daniel E. Kolker
*Assistant Examiner*—Stacey MacFarlane
(74) *Attorney, Agent, or Firm*—Wenderoth, Lind & Ponack, L.L.P.

(57) ABSTRACT

The present invention provides a segment of glycosylation-deficient HGF having mutation(s) introduced into an amino acid sequence so as to prevent glycosylation at at least one glycosylation site of a hepatocyte growth factor (HGF), and a method of producing the same. The segment of glycosylation-deficient HGF of the present invention has the same activity as that of a segment of glycosylated HGF, therefore, it is useful as an alternate for a segment of glycosylated HGF.

10 Claims, 4 Drawing Sheets

Lane 1: Glycosylated NK4
Lane 2: Glycosylation-deficient NK4

SEGMENT OF GLYCOSYLATION-DEFICIENT HGFALPHA-CHAIN

BACKGROUND OF THE INVENTION

1. Field of the Invention

The present invention relates to a modified product of a segment of HGF (hepatocyte growth factor) used for preventing and treating cancers or diseases caused by excessive neovascularization. More specifically, the present invention relates to a segment of HGF, modified by deficiency of glycosylation.

2. Description of the Related Art

For therapy of cancers, surgical therapy, chemotherapy, radiation therapy or multidisciplinary therapy combining them and the like are conducted, however, remarkable anticancer methods are not established yet. Though a primary tumor can be removed by surgical therapy, there is often formation of invisible small metastatic cancers when the cancer is found in the case of cancers showing a tendency of metastasis such as pancreatic and lung cancers, even if the size of the primary tumor is small, and surgical removal thereof is difficult. In chemotherapy and radiation therapy using an anticancer agent, it is difficult to prevent recurrence of a resistant cancer and metastasis of survived cancer cells although the primary tumor may be temporarily decreased in size. With an anticancer agent and radiation therapy, killing also normal cells in addition to cancer cells is accompanied by severe side effects, resulting in decrease in the quality of life and immune power of a patient. Thus, there is currently no method of efficiently preventing cancer metastasis, and there is a strong desire for development of drugs effective for preventing cancer metastasis.

There are a lot of researches conducted in the past regarding the mechanisms of cancer metastasis. Many cancers develop in epithelial tissue, and cancer cells are released from a primary tumor, break a basement membrane partitioning epithelial tissue, invade into surrounding tissues, enter blood and lymphatic vessels and are carried to distal tissues by blood and lymph flow, and again manifest invasion into tissues from blood and lymphatic vessels and growth therein associated with neovascularization.

For suppressing cancer metastasis, it is believed advantageous to inhibit any of these processes, and listed as cancer metastasis suppressing agents are, for example, substances suppressing adhesion of cancer cells with vascular endothelial cells at metastasis site (see non-patent literature 1), neovascularization inhibitors (see non-patent literature 2), substances suppressing invasion of cancer cells (see patent literature 1), substances inhibiting enzymes which degrade basement membranes (see patent literature 2, non-patent literature 3) and the like.

Recently, tumor dormacy therapy is attracting attention regarding cancer therapy. The tumor dormacy therapy makes a dormant condition of cancer cells using a neovascularization inhibitor. The neovascularization inhibitor does not directly kill cancer cells but inhibits neovascularization to block a route for feeding oxygen and nutrition necessary for growth of cancer cells, which results in inducing apoptosis and making a dormant condition of cancer cells. Known as the neovascularization inhibitor are Angiostatin (see non-patent literature 2), Endostatin (see non-patent literature 4), and the like.

Neovascularization occurs by proliferation of capillary vessels of preexisting blood vessels. Neovascularization is indispensable for many physiological processes such as embryogenesis, wound healing, tissue and organ regeneration, while abnormal neovascularization occurs under pathogenic conditions such as tumor growth and at metastatic tumor sites. Initiation of tumor neovascularization is known to be induced by vascular endothelial cell growth factor (VEGF), basic fibroblast growth factor (bFGF), HGF (HGF; Hepatocyte growth factor) and the like.

In addition to such a neovascularization action, HGF has a mitogenic activity, motogenic activity and morphogenic activity, and originally works as a regeneration factor supporting natural healing power of a living body. It is known that various biological activities of HGF are expressed through binding of HGF to a c-Met/HGF receptor on a target cell. The c-Met/HGF receptor is known to be often excessively expressed in many cancer cells (see non-patent literatures 5 to 7), and HGF induces invasion and metastasis of tumor cells (see non-patent literature 8). Cancer cells invade and metastasize by utilizing the actions of HGF owned by a living body through mutual interactions with interstitial cells surrounding the cancer cells (see non-patent literatures 8, 9). Therefore, it is supposed that if binding of HGF to a c-Met/HGF receptor on tumor cells is inhibited, invasion and metastasis of the tumor cells can be suppressed.

NK4 is a protein composed of an N-terminal hairpin domain and four kringle domains of an α-chain of HGF. NK4 binds to a c-Met/HGF receptor and acts as an antagonist against HGF (see non-patent literatures 10, 11). NK4 is known to suppress invasion and metastasis of a tumor by an HGF antagonist activity. Further, NK4 is known to suppress neovascularization induced not only by HGF but also by VEGF and bFGF by a mechanism other than an HGF antagonist activity (see non-patent literature 12). Thus, NK4 is a bi-functional molecule having an HGF antagonist activity and a neovascularization inhibitory activity simultaneously, and NK4 is expected to be utilized as a novel anticancer agent.

Further, NK4 can be expected, based on its neovascularization inhibitory activity, to be also utilized as an agent for preventing or treating various diseases ascribable to blood vessel abnormal proliferation, for example, rheumatic arthritis, diabetic retinopathy, immature infant retinophathy, senile macular degeneration, excess scar formation in wound healing and the like. As described above, neovascularization is indispensable for maintaining metabolism of tissues under normal condition and keeping functional homeostasis of a living body, however, it is known that abnormal neovascularization is related with various diseases including inflammatory diseases. For example, it has been reported that metastasis and recurrence of solid tumors and diseases such as proliferative diabetes, psoriasis vulgaris, rheumatic arthritis, diabetic retinopathy, senile macular degeneration, excess scar formation in wound healing are ascribable to abnormal proliferation of blood vessels, particularly, peripheral capillary vessels (see non-patent literatures 13 and 14). NK4 having a neovascularization inhibitory activity is promising as an agent for preventing or treating such diseases.

Further, NK4 can be expected to provide application as a drug for infection prevention and treatment of *Listeria* and malaria. It is known that a c-Met/HGF receptor is used as a base for human infection with *Listeria monocytogenes* (see non-patent literature 15). Furthermore, activation of a c-Met/HGF receptor by HGF is known to be essential for the initial mechanism of human infection with malaria parasite (see non-patent literature 16). Therefore, it is believed that NK4, an antagonist against HGF, manifests an effect of prevention and treatment of these infectious diseases.

It is necessary to mass-produce an NK4 protein using cells by genetic engineering methods for use, as a pharmaceutical preparation, of an NK4 protein exerting an effect of prevention and treatment of various diseases, as described above. Conventionally, it is known that NK4 can be produced using animal cells such as Chinese hamster ovary (CHO) cells (see patent literature 3), however, in general, methods of producing a protein using animal cells such as CHO cells are expensive, indicating resultant increase in drug price.

As a method of producing a recombinant protein at low cost, known is a method of introducing the intended gene into a prokaryote such as E. coli and allowing this to express (see non-patent literature 17). However, there is a problem that a sugar chain cannot be added to the recombinant protein produced in a prokaryote such as E. coli. The reason for this is that a prokaryote such as E. coli does not contain an endoplasmic reticulum and Golgi apparatus which are places for biosynthesis of a sugar chain.

Addition of a sugar chain to a protein and its modification in an animal cell is post-translational modification using no template, differing from the case of biosynthesis of DNA or proteins. This post-translational modification is conducted through a complicated mechanism via a lot of glycosylation-related enzymes locally present in cell organellas called endoplasmic reticulum and Golgi apparatus. That is, according to a complicated biosynthetic pathway catalyzed by enzymes (glycosidases and glycosyltransferases) specific to certain linkages of monosaccaharides, a sugar chain is elongated so as to obtain a given structure while being subjected to sequential cutting and addition of monosaccharides (see non-patent literature 18). It is known that sugar chains thus added to proteins are widely involved in whole life phenomenon in higher organisms (see non-patent literatures 19, 20).

It is known that half or more of proteins in a human body are present in the form of a glycoprotein carrying sugar chains (see non-patent literature 21), and if a glycoprotein originally present in the form carrying sugar chains is converted into a form containing no sugar chain, there is a fear of losing activity. For example, it is known that erythropoietin known as an erythropoietic hormone loses pharmaceutical activities when sugar chains are removed (see non-patent literature 22).

Yeast is known as a cell which is a host capable of producing a recombinant protein at low cost and having a glycosylation ability (see non-patent literatures 23 to 25). Since yeast is a eukaryote and has an endoplasmic reticulum and Golgi apparatus, it is consequently equipped with glycosylation mechanism. However, since the glycosylation mechanism of yeast differs significantly from that of animal cells, when a protein having glycosylation site(s) is produced in yeast, sugar chain(s) of yeast type would be added. The sugar chain structures of yeast differ significantly from those of other mammals (see non-patent literature 26), and such a recombinant protein manifests antigenicity against human and other mammals, therefore, it cannot be used as a medicament for human and animals.

Further, an insect cell is also a host having a glycosylation ability and can produce a protein at relatively low cost, however, the sugar chain structures of an insect cell are also different from those of human type (see non-patent literature 27), and there is a possibility for a recombinant protein derived from insect cells to show antigenicity against human and other mammals.

Then, one can envisage production of a protein containing no sugar chains by removal of sugar chains from a protein produced using yeast and insect cells and the like, or by introduction of a gene designed to have mutation(s) at glycosylation sites in a protein molecule into yeast and insect cells and the like. However, if a protein originally present in the form carrying sugar chains is converted into a protein containing no sugar chain, there is a fear of losing activity, as described above.

NK4 is a fragment of an HGF α-chain and contains three glycosylation sites of an HGF α-chain (see non-patent literatures 28 and 29). There is utterly no information regarding whether or not NK4 has an activity when sugar chains are removed from NK4.

(Patent Literature 1)
  JP-A No. 3-31214
(Patent Literature 2)
  JP-A No. 5-194414
(Patent Literature 3)
  JP-A No. 2003-250549
(Non-Patent Literature 1)
  Iwamoto Y, et al., Science, 1987, p. 1132-1134
(Non-Patent Literature 2)
  Cao Y, et al., The Journal of clinical investigation, 1988, vol. 101, p. 1055-1063
(Non-Patent Literature 3)
  Irimura T, et al., Biochemistry, 1989, vol. 25, p. 5322-5328
(Non-Patent Literature 4)
  Blezinger P, et al., Nature Biotechnology, 1999, vol. 17, p. 343-348
(Non-Patent Literature 5)
  Di Renzo, et al., Oncogene, 1991, vol. 6, p. 1997-2003
(Non-Patent Literature 6)
  Di Renzo, et al., Cancer research, 1995, vol. 55, p. 1129-1138
(Non-Patent Literature 7)
  Nakajima M., et al., Cancer, 1999, vol. 85, p. 1894-1902 (1999)
(Non-Patent Literature 8)
  Jiang W. G., et al., Critical reviews in oncology/hematology, 1999, vol. 29, p. 209-248
(Non-Patent Literature 9)
  Nakamura T., et al., Cancer research, 1997, vol. 57, p. 3305-3313
(Non-Patent Literature 10)
  Date K., et al., FEBS letters, 1997, vol. 420, p. 1-6
(Non-Patent Literature 11)
  Date K., et al., Oncogene, 1998, vol. 17, p. 3045-3054
(Non-Patent Literature 12)
  Kuba K., et al., Cancer research, 2000, vol. 60, p. 6737-6743
(Non-Patent Literature 13)
  Polverini P J., Critical reviews in oral biology and medicine, 1995, vol. 6 (no. 3), p. 230-247
(Non-Patent Literature 14)
  Forkman J., Nature medicine, 1995, vol. 1 (no. 1), p. 27-31
(Non-Patent Literature 15)
  Shen Y., et al., Cell, 2000, vol. 103, p. 501-510
(Non-Patent Literature 16)
  Carrolo M., et al., Nature Med, 2003, vol. 9, p. 1363-1369
(Non-Patent Literature 17)
  Swarts J. R., Current opinion in biotechnology, 2001, vol. 12, p. 195-201

(Non-Patent Literature 18)
Kornfeld R., et al., Annual review of biochemistry, 1985, vol. 54, p. 631-664

(Non-Patent Literature 19)
Kobata A., European journal of biochemistry, 1992, vol. 209, p. 483-501

(Non-Patent Literature 20)
Varki A., Glycobiology, 1993, vol. 3, p. 97-130

(Non-Patent Literature 21)
Goochee C. F., et al., Biotechnology, 1991, vol. 9, p. 1347-1355

(Non-Patent Literature 22)
Takeuchi M., et al., Glycobiology, 1991, vol. 1, p. 337-346

(Non-Patent Literature 23)
Wiseman A., Endeavour, 1996, vol. 20, p. 130-132

(Non-Patent Literature 24)
Russell C., et al., Australian journal of biotechnology, 1991, vol. 5, p. 48-55

(Non-Patent Literature 25)
Buckholz R. G., et al., Biotechnology, 1991, vol. 9, p. 1067-1072

(Non-Patent Literature 26)
Gemmill T. R., et al., Biochimica et biophysica acta, 1999, vol. 1426, p. 227-237

(Non-Patent Literature 27)
Altmann F., et al., Glycoconjugate journal, 1999, vol. 16, p. 109-123

(Non-Patent Literature 28)
Hara H., et al., Journal of biochemistry, 1993, vol. 114, p. 76-82

(Non-Patent Literature 29)
Shimizu N., et al., Biochemical and biophysical research communications, 1992, vol. 189, p. 1329-1335

SUMMARY OF THE INVENTION

An object of the present invention is to provide a segment of HGF, particularly an HGF α-chain, and an intramolecular fragment of an HGF α-chain, which are modified by glycosylation-deficiency, and a method of producing the same.

The present inventors have intensively studied the sugar chain function of an NK4 protein to solve the above-mentioned problems, and resultantly found that the function of NK4 is kept even if sugar chains of an NK4 protein are removed. It was utterly unexpected that an NK4 protein which is a bi-functional molecule having an HGF antagonist activity and a neovascularization inhibitory activity simultaneously keeps these functions equivalently to glycosylated NK4 even if sugar chains are removed. Based on the above-mentioned findings, the present inventors have further developed investigations and completed the present inventions.

Namely, the present invention relates to (1) A segment of glycosylation-deficient HGF, having a deficiency of at least one sugar chain at glycosylation sites of an HGF α chain, and selected from the following proteins (a) to (c), wherein the above-mentioned protein has an N terminal hairpin domain and the subsequent four kringle domains, has an antagonist activity against the action of HGF via a c-Met/HGF receptor, and has a neovascularization inhibitory activity:

(a) a protein having an amino acid sequence from 32nd to 494th in SEQ ID NO: 1,
(b) a protein having an amino acid sequence from 32nd to 494th of SEQ ID No. 1, wherein 1 to 30 amino acids are deleted, substituted, added or inserted in said amino acid sequence,
(c) a protein having a homology of at least 80% or higher with amino acids from 32nd to 494th of SEQ ID NO: 1, (2) The segment of glycosylation-deficient HGF according to (1), wherein the amino acid(s) is/are substituted so as to prevent glycosylation at at least one glycosylation site of the protein, (3) The segment of glycosylation-deficient HGF according to (2), wherein the substitution(s) of amino acid(s) is/are at least one of the following (a) to (d):

(a) Asn of at least one N-glycosylation site is substituted by another amino acid, wherein N-glycosylation site means a portion having consensus sequence represented by the amino acid sequence Asn-X-Ser or Asn-X-Thr wherein X represents an amino acid other than Pro.

(b) Ser or Thr of one N-glycosylation site, or Ser and/or Thr of two or more N-glycosylation sites, is/are substituted by another amino acid, wherein N-glycosylation site means a portion having consensus sequence represented by the amino acid sequence Asn-X-Ser or Asn-X-Thr wherein X represents an amino acid other than Pro.

(c) X of at least one N-glycosylation site is substituted by Pro, wherein N-glycosylation siite means a portion having consensus sequence represented by the amino acid sequence Asn-X-Ser or Asn-X-Thr wherein X represents an amino acid other than Pro, and (d) at least one of Ser and Thr which undergoes O-glycosylation is substituted by another amino acid.

(4) The segment of glycosylation-deficient HGF according to (2), wherein the substitution(s) of amino acid(s) is/are at least one of the following (a) to (d):

(a) amino acid(s) at 294th and/or 296th of an amino acid sequence of SEQ ID NO: 1 is/are substituted by another amino acid, and/or an amino acid at 295th thereof is substituted by Pro, leading thereby to no glycosylation at 294th, (b) amino acid(s) at 402nd and/or 404th of an amino acid sequence of SEQ ID NO: 1 is/are substituted by another amino acid, and/or an amino acid at 403rd thereof is substituted by Pro, leading thereby to no glycosylation at 402nd, or (c) an amino acid at 476th of an amino acid sequence of SEQ ID NO: 1 is substituted by another amino acid, leading thereby to no glycosylation at 476th, (5) The segment of glycosylation-deficient HGF according to any one of (1) to (4), wherein amino acids at 162nd to 166th of an amino acid sequence of SEQ ID NO: 1 are deleted, and (6) The segment of glycosylation-deficient HGF according to any one of (1) to (5), wherein amino acids at 479th to 494th of an amino acid sequence of SEQ ID NO: 1 are deleted.

Further, the present invention relates to (7) A DNA comprising a base sequence coding the segment of glycosylation-deficient HGF according to any one of (1) to (6), (8) A vector containing the DNA according to (7) incorporated therein, (9) A method of producing the segment of glycosylation-deficient HGF according to any one of (1) to (6), comprising introducing the vector according to (8) into a cell, culturing the cell, allowing a segment of glycosylation-deficient HGF to be accumulated in the cell or to be secreted into culture solution of the cell, and collecting and purifying the segment of glycosylation-deficient HGF from the cell or culture solution of the cell,

(10) The method of producing the segment of glycosylation-deficient HGF according to (9), wherein the cell is a eukaryotic cell,

(11) The method of producing the segment of glycosylation-deficient HGF according to (10), wherein the eukaryotic cell is a yeast or insect cell,

(12) A method of producing the segment of glycosylation-deficient HGF according to any one of (1) to (6), comprising introducing the vector according to (8) into an insect individual, allowing a segment of glycosylation-deficient HGF to be accumulated in the insect individual, and collecting and purifying the segment of glycosylation-deficient HGF from the insect individual,

(13) A method of producing the segment of glycosylation-deficient HGF according to any one of (1) to (6), comprising treating a segment of HGF having sugar chain(s) with an enzyme to remove the sugar chain(s) wholly or partially, and collecting and purifying the segment of glycosylation-deficient HGF from the enzymatic reaction mixture,

(14) A method of producing the segment of glycosylation-deficient HGF according to any one of (1) to (6), comprising introducing a vector containing an incorporated DNA coding a segment of HGF having sugar chain(s) or the vector according to (8) into a cell having no glycosylation ability, culturing the cell, allowing a segment of glycosylation-deficient HGF to be accumulated in the cell or to be secreted into culture solution of the cell, and collecting and purifying the segment of glycosylation-deficient HGF from the cell or culture solution of the cell,

(15) A method of producing the segment of glycosylation-deficient HGF according to any one of (1) to (6), comprising synthesizing a segment of glycosylation-deficient HGF by cell-free protein synthesis system using a DNA having a base sequence coding a segment of HGF having sugar chain(s) or the DNA according to (7) as a template, and collecting and purifying the segment of glycosylation-deficient HGF from the synthesis reaction mixture,

(16) A method of producing the segment of glycosylation-deficient HGF according to any one of (1) to (6), comprising limited digestion of glycosylation-deficient HGF which lacks at at least one or all of glycosylation sites, by treatment with a protease or by chemical treatment of HGF, and collecting and purifying the segment of glycosylation-deficient HGF from the treatment solution, and

(17) The method of production according to (16), wherein the protease is an esterase.

Still further, the present invention relates to

(18) An agent comprising the segment of glycosylation-deficient HGF according to any one of (1) to (6) as an active ingredient,

(19) The agent according to (18), wherein the agent is a neovascularization inhibiting agent,

(20) The agent according to (18), wherein the agent is an antagonist against the action of HGF via a c-Met/HGF receptor,

(21) The agent according to any one of (18) to (20), wherein the agent is an agent suppressing invasion, growth or metastatis of a tumor,

(22) The agent according to any one of (18) to (20), wherein the agent is an apoptosis inducing agent,

(23) The agent according (20), wherein the agent is an agent for prevention and/or treatment of an infectious disease,

(24) The agent according to (23), wherein the infectious disease is an infectious disease caused by a malaria or *Listeria* parasite, and

(25) A gene pharmaceutical composition, comprising the DNA according to (7).

Furthermore, the present invention relates to use of a segment of a glycosylation-deficient HGF for producing a pharmaceutical preparation for inhibiting neovascularization and the like, and a method of preventing and treating neovascularization and the like by administrating an agent containing a segment of a glycosylation-deficient HGF as an active ingredient to a patient. Also, the present invention relates to a use of DNA coding a segment of a glycosylation-deficient HGF for producing a gene pharmaceutical composition for inhibiting neovascularization and the like, and a method of preventing and treating neovascularization and the like by administrating a gene pharmaceutical composition containing DNA coding a segment of a glycosylation-deficient HGF to a patient.

The segment of a glycosylation-deficient HGF of the present invention (hereinafter, abbreviated as segment of glycosylation-deficient HGF) can be produced by the use of yeast or insect cells, and therefore, a segment of a glycosylation-deficient HGF can be produced at low cost. Particularly, it is significant to be able to produce glycosylation-deficient NK4 at low cost.

Since the segment of a glycosylation-deficient HGF of the present invention (for example, glycosylation-deficient NK4) is equivalent to a segment of HGF having sugar chain(s) (for example, NK4 having sugar chain(s)) with regard to an HGF antagonist activity, neovascularization inhibitory activity and the like, it can be an alternate for a segment of HGF having sugar chain(s) (for example, NK4 having sugar chain(s)). That is, the segment of a glycosylation-deficient HGF of the present invention can be used for suppressing_invasion, suppressing growth, suppressing_metastasis, inducing apoptosis and/or suppressing neovascularization of tumor cells. An agent containing DNA coding a segment of a glycosylation-deficient HGF of the present invention can be used as a gene pharmaceutical composition.

DETAILED DESCRIPTION OF THE PREFERRED EMBODIMENTS

Figure 1:
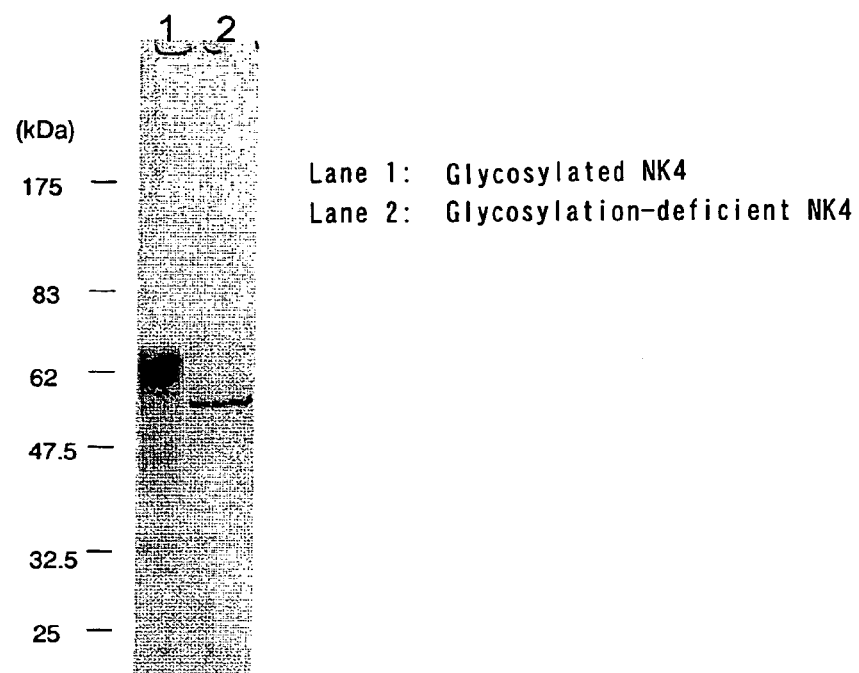
FIG. 1 is a view showing results of analysis of glycosylated NK4 and glycosylation-deficient NK4 by SDS-PAGE.

The present invention will be illustrated in detail below.

In the present invention, "a segment of a glycosylation-deficient HGF" means a segment of HGF in which all or at least one sugar chain at glycosylation sites of an HGF α-chain, preferably all sugar chains, are deficient. "Segment of HGF" means, for example, an α-chain protein of HGF of human and mammals (for example, dogs, cats, cattle, horses, pigs, sheep, etc.), having an amino acid sequence in 32nd to 494th of SEQ ID NO: 1 and having an N-terminal hairpin domain and the subsequent four kringle domain structures, or a protein of an intramolecular fragment of HGF having the above-mentioned N-terminal hairpin domain and the subsequent four kringle domains, preferably a protein of an intramolecular fragment of an HGF α-chain. As the protein of an intramolecular fragment of an HGF α-chain, listed are proteins obtained from an HGF α-chain (for example, 32nd to 494th of SEQ ID NO: 1) by deletion of 1 to 30, preferably 1 to 25, more preferably 1 to 21 amino acids. Specifically listed is a 5 amino acid-deleted type HGF α-chain represented by 32nd to 489th of SEQ ID NO: 2, being obtained by deletion of 162nd to 166th amino acids of SEQ ID NO: 1, for example. Further listed are NK4 represented by an amino acid sequence in 32nd to 478th of SEQ ID NO: 1 (479th to 494th amino acids are deleted in an amino acid sequence represented by SEQ ID NO: 1), and NK4 represented by an amino acid sequence in 32nd to 473rd of SEQ ID NO: 2 (474th to 489th amino acids are deleted in an amino acid sequence represented by SEQ ID NO: 2), for example.

In the segment of a glycosylation-deficient HGF of the present invention, the protein having an amino acid sequence obtained from an HGF α-chain (for example, 32nd to 494th of SEQ ID NO: 1) by deletion, substitution, addition or insertion of 1 to 30, preferably 1 to 25 amino acids means a protein obtained by deletion, substitution, addition or insertion of amino acids by genetic engineering methods and/or spontaneous mutation and the like. Specifically mentioned are proteins of an intramolecular fragment of an HGF α-chain described above, proteins obtained by addition of amino acid(s) to N-terminal and/or C-terminal of an HGF α-chain, and/or proteins obtained by deletion, substitution, addition or insertion and the like of amino acid(s) of glycosylation site(s) of an HGF α-chain by genetic engineering methods so as to inhibit glycosylaton. Proteins obtained by deletion, substitution, addition or insertion and the like of amino acid(s) by using well-known techniques such as site-directed mutagenesis methods, and proteins naturally produced by deletion, substitution, addition or insertion and the like of amino acid(s) of a number 1 to several are also included.

Also included are proteins having a homology of 80% or more, preferably 85% or more, more preferably 90% or more with an amino acid sequence of an HGF α-chain in a segment of a glycosylation-deficient HGF of the present invention. In the present invention, "homology" means the extent of coincidence of amino acid residues constituting respective sequences when primary structures of proteins are compared.

Those having a modified amino acid residue, pyroglutamic acid, as the N-terminal amino acid of a protein are also included in the segment of a glycosylation-deficient HGF of the present invention.

The segment of a glycosylation-deficient HGF of the present invention is a protein having an antagonist activity against the action of HGF mediated via a c-Met/HGF receptor and having a neovascularization inhibitory activity. Listed as the action of HGF mediated via a c-Met/HGF receptor are a tyrosine phosphorylation of a c-Met/HGF receptor, motogenic activity, mitogenic activity and morphogenic activity (Matsumoto K. and Nakamura T., Biochem. Biophys. Res. Commun., 1997, vol. 239, p. 639-644). The neovascularization inhibiting action preferably means an action of inhibiting neovascularization in which HGF, FGF and VEGF are involved though its mechanism is not critical when it is an action inhibiting neovascularization.

Deficiency of sugar chain(s) of a segment of HGF can be generated by introducing mutation(s) into a base sequence to cause deletion, substitution and addition of amino acid(s) in an amino acid sequence so as to prevent addition of sugar chain(s) preferably at at least one of glycosylation sites of an HGF α-chain, however, deficiency can also be caused by treating a segment of HGF having sugar chain(s) with some enzymes.

As the method of introducing mutation(s) into a gene of a segment of HGF so as to prevent addition of sugar chain(s) at at least one of glycosylation sites of an HGF α-chain, it is advantageous to introduce mutation(s) into a base sequence coding glycosylation site to be made deficient.

Two types of sugar chains are known. One is an N-linked type sugar chain and the other is an O-linked type sugar chain. The following mutations are introduced into a base sequence, respectively.

In the case of the N-linked type sugar chain, a consensus sequence (Asn-X-Ser or Asn-X-Thr (X represents an amino acid other than proline)) subjected to glycosylation is known. In the case of the presence of a consensus sequence, a sugar chain is added to Asn in the consensus sequence (Kobata A., Eur. J. Biochem., 1992, vol. 209, p. 483-501). Therefore, an N-linked type sugar chain can be made deficient by introducing mutation(s) into a base sequence so as to convert Asn in a consensus sequence into another amino acid (for example, Gln and the like), or to convert Ser or Thr in the consensus sequence into another amino acid (for example, Gly, Ala and the like). In this case, it is preferable to appropriately select an amino acid for conversion so as not to form a new consensus sequence with backward and forward amino acid sequences of the above-mentioned consensus sequence. It may also be permissible to introduce mutation(s) into a base sequence so that proline is introduced at X site in a consensus sequence.

In the case of the O-linked type sugar chain, a sugar chain is added to a hydroxyl group of Ser or Thr in an O-glycosylation site, however, a consensus sequence for O-glycosylation does not exist. A sugar chain at the O-glycosylation site can be made deficient by introducing mutation(s) into a base sequence so as to convert Ser or Thr subjected to O-glycosylation into another amino acid (for example, Gly and the like). In this case, it is preferable to appropriately select an amino acid for conversion so as not to form a consensus sequence for N-glycosylaton with backward and forward amino acid sequences of the amino acid.

Glycosylation-deficient site(s) of a segment of a glycosylation-deficient HGF coincides with glycosylation site(s) of a segment of HGF, and in NK4 as a segment of an intramolecular fragment of an α-chain of human HGF having an amino acid sequence from 32nd to 478th of SEQ ID NO: 1 for example, they are Asn (N-linked type) at 294th, Asn (N-linked type) at 402nd and Thr (O-linked type) at 476th. Glycosylation site(s) in NK4 as an intramolecular fragment of an α-chain of 5 amino acid-deleted human HGF having an amino acid sequence from 32nd to 473rd of SEQ ID NO: 2 (hereinafter, abbreviated as 5 amino acid-deleted NK4) is/are Asn (N-linked type) at 289th, Asn (N-binding type) at 397th and Thr (O-linked type) at 471st of SEQ ID NO.: 2. The above-mentioned consensus sequence for N-glycosylation in the above-mentioned NK4 is present at from 294th to 296th and from 402nd to 404th of an amino acid sequence of SEQ ID NO: 1, and in the 5 amino acid-deleted NK4, the consensus sequence for N-glycosylation is present at from 289th to 291st and from 397th to 399th in an amino acid sequence of SEQ ID NO: 2.

Regarding the method of introducing mutation(s) into a base sequence, when, for example, mutatons are introduced into DNA coding NK4, mutagenic primers corresponding to a portion into which mutations are to be introduced are synthesized, and introduction can be conducted using a known technology such as a Kunkel method. By using a commercially available mutagenesis kit and the like, mutations can be introduced easily. It is also possible that based on known base sequence information on NK4, a base sequence at portions into which mutations are to be introduced is modified, and DNA is produced by chemical synthesis using a conventionally known method. As the chemical synthesis method, there are listed chemical synthesis methods using DNA synthesizers such as a DNA synthesizer model 392 (manufactured by Perkin Elmer) utilizing a phosphoramidite method.

DNA codng a segment of an HGF α-chain, for example, DNA coding NK4, can be obtained, for example, by a method described in JP-A No. 2003-250549 or according to this method. For example, primers are prepared based on a known HGF base sequence, and DNA is amplified by a PCR method using, as a template, HGF cDNA synthesized from HGF mRNA contained in human tissues or cells or HGF cDNA selected from cDNA library, thereby enabling to obtain DNA coding NK4. It is also possible to amplify cDNA by a RT-PCR method from mRNA contained in human tissues or cells. Further, it can be obtained also by the above-mentioned chemical synthesis.

A recombinant expression vector for a segment of glycosylation-deficient HGF can be constructed from a recombinant vector such as a plasmid and phage containing DNA coding an amino acid sequence of a segment of a glycosylation-deficient HGF, by excising this DNA with a restriction enzyme, and re-connecting it to downstream of a promoter of a vector suitable for expression of a segment of a glycosylation-deficient HGF by using a restriction enzyme and DNA ligase. More specifically, construction is so made that it contains, if necessary, (1) promoter, (2) ribosome binding site, (3) initiation codon, (4) DNA containing a base sequence coding a segment of a glycosylation-deficient HGF of the present invention, (5) termination codon and (6) terminator in this order toward downstream direction of transcription.

By incorporating a secretion signal sequence before a base sequence coding a segment of a glycosylation-deficient HGF, the segment of a glycosylation-deficient HGF can be secreted out of a cell. The signal sequence is preferably to be recognized by a host cell and processed. For example, when the host cell belongs to Escherichia species, signal sequences of PhoA, OmpA and the like can be utilized, when the host cell belongs to Bacillus species, signal sequences of α-amylase, subtilisin and the like can be utilized, when the host cell is yeast, signal sequences of MFα, SUC2 and the like can be utilized, and when the host cell is a mammalian cell, signal sequences of HGF, insulin, α-interferon and the like can be utilized, respectively. In a segment of human HGF, it is particularly preferable to utilize a signal sequence of human HGF. Specifically, a base sequence coding an amino acid sequence 1 to 31 as depicted in SEQ ID NO: 1 corresponds to a signal sequence.

The above-mentioned DNA includes not only DNA composed of a base sequence coding a sequence of a segment of glycosylation-deficient HGF obtained by introducing mutation(s) into the above-mentioned base sequence coding glycosylation site(s), but also (a) DNA having a base sequence having deletion, substitution, addition or insertion of one or more bases in a base sequence coding the above-mentioned sequence of a segment of glycosylation-deficient HGF having an HGF antagonist activity and neovascularization inhibitory activity, (b) DNA hybridizing under stringent conditions with DNA composed of a base sequence complimentary to DNA having a base sequence coding the above-mentioned sequence of a segment of a glycosylation-deficient HGF having an HGF antagonist activity and neovascularization inhibitory activity, (c) DNA having a homology of at least 80% or more with DNA having a base sequence coding the above-mentioned sequence of a segment of glycosylation-deficient HGF having an HGF antagonist activity and neovascularization inhibitory activity.

"Deletion, substitution, addition or insertion of one or more bases" regarding the above-mentioned base sequences means deletion, substitution, addition or insertion and the like of bases of a number 1 to several, which can be introduced by well-known technological methods such as a site-directed mutagenesis method or can be introduced naturally.

DNA hybridizable under stringent conditions means DNA obtained by a colony hybridization method, plaque hybridization method, southern blot hybridization method and the like using the above-mentioned DNA as a probe.

The stringent conditions mean hybridization conditions, for example, SSC solution of about 0.1 to 2-fold concentration (SSC solution at 1-fold concentration contains 150 mM sodium chloride and 15 mM sodium citrate) at temperatures of about 65° C.

DNA having homology means DNA showing a homology of at least about 80% or more under high stringent conditions, preferably DNA having a homology of about 85% or more, more preferably DNA having a homology of about 90% or more. The high stringent conditions include, for example, a sodium concentration of about 19 to 40 mM, preferably about 19 to 20 mM, and a temperature of about 50 to 70° C., preferably about 60 to 65° C. Particularly, a sodium concentration of about 19 mM and a temperature of about 65° C. are most preferable conditions.

As the vector which can be used in the present invention, plasmids such as pBR 322, pUC18, pUC19 (Toyobo Co. Ltd.) can be used in the case of Escherichia coli as a host, plasmids such as pUB110 (Sigma) can be used in the case of Bacillus subtilis as a host, and plasmids such as pYES2 (Invitrogen), pRB15 (ATCC 37062) can be used in the case of yeast as a host. As the expression vector for animal cells, listed are pCAGGS and pCXN2 (Niwa H., Yamamura K. and Miyazaki J., Gene, 1991, vol. 108, p. 193 to 200, JP-A No. 03-168087), pcDL-SRα (Takebe Y., et al., Mol. Cell. Biol., 1988, vol. 8, p. 466-472) and the like. Additionally, bacteriophage λgt10, λgt11 (Stratagene), vector derived from a gene of SV40 (BRL), BPV (ATCC VR-703), retrovirus and the like are listed, however, there is no specific restriction providing they are vectors capable of replicating and amplifying in a host.

Also regarding promoters and terminators, there is no specific restriction so long as they work in a host used for expression of a base sequence coding an intended segment of a glycosylation-deficient HGF. As the promoter, listed are trp promoter, lac promoter, recA promoter, λPL promoter, lpp promoter and the like in the case of Escherichia coli as a host, and listed are PHO5 promoter, PGK promoter, GAP promoter, ADH promoter and the like in the case of yeast as a host. When animal cells are used as a host, promoters obtained from virus genomes such as Rous sarcoma virus (virus RSV), MPSV, polyoma virus, fowlpox virus, adenovirus, bovine papilloma virus, fowl sarcoma virus, cytomegalovirus (CMV), hepatitis B virus, simian virus 40 (SV40), and vaccinia virus; metallo-thioneine promoter; heat shock promoter; and the like are listed. In the case of using a higher mammal host, an enhancer is preferably introduced into a vector. By introducing an enhancer, transcription increases. Listed as the enhancer are SV40 enhancer, initial promoter/enhancer of cytomegalovirus, polyoma enhancer, adenovirus enhancer and the like. As the terminator, listed are trp terminator, lpp terminator and the like in the case of *Escherichia coli* as a host, listed are amyF terminator and the like in the case of *Bacillus subtilis* as a host, listed are CYC1 terminator and the like in the case of yeast as a host, and listed are SV40 terminator, HSV1TK terminator and the like in the case of animal cells as a host. These promoters and terminators are appropriately combined depending on the host used.

The cell which can be used as a host is not particularly restricted, and eukaryotic cells such as animals, plants, insects, eukaryotic microorganisms and the like, and prokaryotic cells such as prokaryotic microorganisms and the like are listed. These cells may form an individual, and animal individuals, plant individuals and insect individuals may be used as a host. The eukaryotic cell may be an adherent cell or floating cell, for example, may be a eukaryotic cell producing and accumulating a segment of HGF in the cell, or a eukaryotic cell producing and secreting a segment of HGF out of the cell. As the animal cell, for example, CHO cell (Chinese hamster ovary cell), COS cell, BHK cell, mouse C127 cell and Hela cell and the like are listed. As the plant cell, for example, cells of rice, tobacco, *Arabidopsis thaliana* and the like are listed, and as the insect cell, for example, cells of Sf9, Sf21 and the like are listed. As the insect individual, for example, silk worm (*Bombyx mori*) is mentioned. As the eukaryotic microorganism, yeasts such as *Saccharomyces cerevisiae, Schizosaccharomyces pombe, Candida boidinii, Pichia pastoris* and the like, and filamentous fungi such as *Aspergillus, Trichoderma, Mucor* and the like are listed. As the prokaryotic microorganism, *Escherichia coli* and *Bacillus subtilis* and the like are listed, and these prokaryotic cells have no glycosylation ability, therefore, an expression vector coding a segment of HGF containing glycosylation sites may be introduced. Preferable are yeasts, insect cells or insect individuals.

An expression vector for a segment of a glycosylation-deficient HGF is introduced into a host by a competent cell method (J. Mol. Biol., 1970, vol. 53, p. 154), protoplast method (Proc. Natl. Acad. Sci. USA, 1978, vol. 75, p. 1929), calcium phosphate method (Science, 1983, vol. 221, p. 551), DEAE dextran method (Science, 1982, vol. 215, p. 166), electric pulse method (Proc. Natl. Acad. Sci. USA, 1984, vol. 81, p. 7161), in vitro packaging method (Proc. Nat. Acad. Sci. USA, 1975, vol. 72, p. 581), virus vector method (Cell, 1984, vol. 37, p. 1053), micro injection method (Exp. Cell. Res., 1984, vol. 153, p. 347) and the like, to produce a transformant. The resultant transformant is cultured in an appropriate medium corresponding to its host for the purpose of producing an intended segment of a glycosylation-deficient HGF. The medium contains carbon sources, nitrogen sources, inorganic substances, vitamins, serum and medicaments and the like necessary for growth of the transformant. As the medium, LB medium (Nissui Pharmaceutical Co., Ltd.), M9 medium (J. Exp. Mol. Genet., Cold Spring Laboratory, New York, 1972, p. 431) and the like are listed when the host of a transformant is *Escherichia coli*, and YEPD medium (Genetic Engineering, vol. 1, Plenum Press, New York, 1979, p. 117) and the like are listed when the host is yeast. When the host is an animal cell, MEM medium, DMEM medium, RPMI 1640 medium (Nissui Pharmaceutical Co., Ltd.) containing 20% or less fetal bovine serum, and the like are listed. Culturing of a transformant is conducted usually at a temperature of 20 to 45° C. and a pH of 5 to 8, and ventilation and stirring are conducted as required. When the host is animal adherent cell and the like, carriers such as glass beads, collagen beads or acetyl cellulose hollow fiber are used. Culturing of a transformant can be conducted even with a medium composition or under culturing conditions other than the above compositions and conditions so long as the transformant can grow, therefore, the composition and culturing condition are not limited to the above-mentioned examples.

In culturing, when a protease inhibitor is added into culture solution, decomposition of a segment of a glycosylation-deficient HGF can be suppressed, leading to improvement in productivity of the segment of a glycosylation-deficient HGF. As the protease inhibitor to be added, benzamidine, aprotinin, leupeptin, antipain, chymostatin, pepstatin A, phenylmethanesulfonyl fluoride (PMSF), ethylenediamine tetraacetic acid (EDTA) and the like are listed.

The segment of a glycosylation-deficient HGF thus produced in a transformant or the culture supernatant of a transformant can be separated, collected and purified by a known salting out method, solvent precipitation method, dialysis method, ultrafiltration method, gel electrophoresis method or gel filtration chromatography, ion exchange chromatography, reverse phase chromatography, affinity chromatography and the like in combination. Particularly, combinations of a salting out method using ammonium sulfate, S-sepharose ion chromatography, heparin sepharose affinity chromatography and phenylsepharose hydrophobic chromatography, or combinations of a salting out method using ammonium sulfate, S-sepharose ion chromatography and anti-HGF antibody sepharose affinity chromatography, and the like are preferable and effective purification methods.

The segment of a glycosylation-deficient HGF of the present invention can also be prepared by obtaining a segment of glycosylated HGF by conventionally known methods, then, treating the segment of HGF with an enzyme removing a sugar chain. As the enzyme removing a sugar chain, there can be used glycopeptidase F, glycopeptidase A and the like for the purpose of removing an N-linked type sugar chain. Removal of an O-linked type sugar chain can be attained by combining sialidase, fucosidase, O-glycanase and the like. In this case, it is desirable to add a protease inhibitor into the reaction solution. As the protease inhibitor to be added, benzamidine, aprotinin, leupeptin, antipain, chymostatin, pepstatin A, phenylmethanesulfonyl fluoride (PMSF), ethylenediamine tetraacetic acid (EDTA) and the like are listed. The segment of HGF from which a sugar chain is removed by enzymatic treatment can be collected as the segment of a glycosylation-deficient HGF of the present invention and purified by the above-mentioned purification method.

Further, the segment of a glycosylation-deficient HGF of the present invention can be obtained also by utilizing cell-free protein synthesis system. The cell-free protein synthesis system means a method of performing protein synthesis using DNA or mRNA coding the intended protein as a template without using a live cell, while using cell extract prepared from *Escherichia coli*, rabbit reticulocyte, wheat germ and the like or using protein synthesis factors contained in the cell extract solution. Since cell extract solution contains molecules necessary for protein synthesis such as ribosome, tRNA, and translation factor, a protein is synthesized upon addition of an energy source such as ATP, GTP, etc. and amino acids as substrates. Instead of cell extract solution, a mixture of protein synthesis factors contained in cell extract solution may be used. In the cell-free protein synthesis system, a segment of a glycosylation-deficient HGF can be produced using, as a template, DNA or mRNA coding a segment of HGF having glycosylation site(s), because an endoplasmic reticulum and Golgi apparatus are not contained therein. DNA or mRNA having mutation(s) introduced into glycosylation site(s) can also be used.

A protease inhibitor can also be added into the reaction mixture. As the protease inhibitor to be added, benzamidine, aprotinin, leupeptin, antipain, chymostatin, pepstatin A, phenylmethanesulfonyl fluoride (PMSF), ethylenediamine tetraacetic acid (EDTA) and the like are listed. The segment of a glycosylation-deficient HGF synthesized in the cell-free protein synthesis reaction mixture can be collected and purified by the above-mentioned purification method.

The segment of a glycosylation-deficient HGF of the present invention can be produced also by digesting glycosylation-deficient HGF with a protease, or by specifically cutting this by chemical treatment. Glycosylation-deficient HGF used for this purpose can be produced by introducing mutation(s) into glycosylation site(s) of HGF based on an already known gene sequence of HGF. Enzymatic digestion of glycosylation-deficient HGF can be conducted using a specific protease such as, for example, elastase, HGF activator, urokinase type plasminogen activator, matriptase, etc. The segment of a glycosylation-deficient HGF generated can be collected and purified by the above-mentioned purification method.

The segment of a glycosylation-deficient HGF of the present invention obtained as described above has an activity equivalent to that of the segment of a glycosylated HGF in an antagonist activity against the action of HGF mediated via a c-Met/HGF receptor and a neovascularization inhibitory activity.

The segment of a glycosylation-deficient HGF of the present invention is effective as a pharmaceutical product, and used in the form of general pharmaceutical preparation. The pharmaceutical preparation containing the segment of a glycosylation-deficient HGF of the present invention as an active ingredient can adopt various dosage forms (for example, liquid, solid, capsule and the like), and in general, the segment of a glycosylation-deficient HGF as an active ingredient is used in combination with a pharmaceutically acceptable carrier to give an injection, inhalant, suppository or oral agent, and an injection is suitable. This injection can be prepared by a normal method, and for example, can be prepared by dissolving a segment of a glycosylation-deficient HGF and a pharmaceutically acceptable carrier into a suitable solvent (for example, sterile purified water, buffer solution, physiological saline solution and the like), then, filtrating the solution through a filter and the like for sterilization, then, filling this in a sterile vessel. The amount of a segment of a glycosylation-deficient HGF in an injection is usually adjusted from about 0.0002 to 3 (w/v %), preferably from 0.001 to 2 (w/v %). The oral drug is formulated into a dosage form such as, for example, tablet, granule, fine granule, powder, soft or hard capsule, liquid, emulsion, suspension, syrup and the like, and these preparations can be prepared by an ordinary method for preparation. The suppository can also be prepared by an ordinary method for preparation using a conventional base (for example, cacao butter, lauric butter, glycerogelatine, Macrogol, Witepsol and the like). The inhalant can also be prepared according to normal means for preparation. The amount of a segment of a glycosylation-deficient HGF in a preparation can be appropriately adjusted depending on dosage form, disease to be treated and the like.

In the formulation of a pharmaceutical preparation of the segment of a glycosylation-deficient HGF of the present invention, a stabilizer is preferably added. As the stabilizer, for example, albumin, globulin, gelatin, alanine, glycine, mannitol, glucose, dextran, sorbitol, ethylene glycol and the like are listed. The pharmaceutical preparation of the present invention may contain necessary other additives, for example, solvents (for example, physiological saline solution, sterile purified water, injectable water and the like), excipients (for example, fructose, D-sorbitol, glucose, starch, crystalline cellulose, dextrin and the like), binders (for example, gelatin, corn starch, tragacanth, gum arabic and the like), solubilizers (for example, lauromacrogol, Polysorbate 80, polyoxyethylene hardened castor oil 60, gum arabic, sodium benzoate and the like), antioxidants (for example, L-ascorbic acid, tocopherol, sodium edetate and the like), soothing agents (for example, benzalkonium chloride, procaine hydrochloride and the like), isotonic agents (for example, sodium chloride, glucose, D-mannitol, glycerin and the like), buffers (for example, citric acid, sodium citrate, acetic acid, sodium acetate, lactic acid, sodium hydrogenphosphate and the like), thickening agents (gum arabic, carmellose, popidone, methylcellulose and the like), preservatives (for example, methyl α-oxybenzoate, ethyl α-oxybenzoate, propyl α-oxybenzoate, chlorobutanol, benzyl alcohol, benzalkonium chloride and the like), pH adjusters (hydrochloric acid, sodium hydroxide, citric acid, acetic acid and the like), and the like.

In the case of liquid preparation, it is preferable to retain the preparation by cryopreservation, or by lyophilization and the like to remove moisture. In the case of a lyophilized preparation, injectable distilled water and the like are added before its use to reconstitute the preparation.

In the case of oral preparation, it is preferable to apply a film of an enteric coating agent (for example, cellulose acetate phthalate, methacrylic acid copolymer, hydroxypropylcellulose phthalate, carboxymethylethyl cellulose and the like) and the like to make a granule, tablet and the like, and in the case of capsule, an enteric coated capsule is preferable.

The preparation of the present invention can be administered via a suitable administration route corresponding to its dosage form. For example, it can be made into a form of injection and administered intravenously, intraarterially, subcutaneously, intramuscularly, etc. The dose thereof is appropriately adjusted depending on disease, symptom, age, body weight and the like of a patient, and for example, it is from 0.01 mg to 500 mg, preferably from 0.05 mg to 100 mg in adults in the case of a segment of a glycosylation-deficient HGF (for example, glycosylation-deficient NK4), and once daily administration or several times daily administration is suitable.

The segment of a glycosylation-deficient HGF of the present invention can be used for suppressing invasion, suppressing growth, suppressing metastasis, inducing apoptosis and/or inhibiting neovascularization of tumor. Therefore, an agent containing the segment of a glycosylation-deficient HGF of the present invention can be used as an agent for preventing and treating a cancer and/or a disease caused by neovascularization, and an agent for preventing metastasis of cancer.

Examples of the target cancers include lung cancer, ovarian cancer, pancreatic cancer, stomach cancer, gallbladder cancer, kidney cancer, prostatic cancer, breast cancer, esophageal cancer, liver cancer, oral cavity cancer, colon cancer, large bowel cancer, uterine cancer, bile duct cancer, islet cell carcinoma, adrenocortical cancer, bladder cancer, testis cancer, testicular tumor, thyroid cancer, skin cancer, malignant carcinoid tumor, malignant melanoma, osteosarcoma, soft tissue sarcoma, neuroblastoma, Wilms tumor, retinoblastoma, melanoma, glioma and the like, and of them, ovarian cancer, pancreatic cancer, stomach cancer, gallbladder cancer, kidney cancer, prostatic cancer, breast cancer, esophageal cancer, liver cancer, oral cavity cancer, colon cancer, large bowel cancer, sarcoma, melanoma and glioma are preferable, and particularly, ovarian cancer, pancreatic cancer, stomach cancer and gallbladder cancer are preferable.

An agent containing the segment of a glycosylation-deficient HGF of the present invention can be used in combination with other anticancer agent and the like. As the other anticancer agent, there are listed, for example, alkylating agents (for example, nitrogen mustard, merphalan, cyclophosphamide, chlorambucil, thiotepa, dibromomannitol, dibromodulcitol, carmustine, lomustine, semustine, nimustine hydrochloride, chlorozotocine, ranimustine, busulphan, procarbazine and the like), various antimetabolites (for example, 6-mercaptopurine, azathioprine, 6-thioguanine, thioinosine, fluorouracil, tegafur, carmofur, doxifluridine, broxuridine, cytarabine, enocitabine, methotrexate, trimethotrexate and the like), antitumor antibiotics (for example, daunorubicin, aclarubicin, doxorubicin, actinomycin D, mitomycin C, bleomycin, peplomycin and the like), other antitumor agents (for example, cisplatin, carboplatin, tamoxifen, L-asparaginase, aceglaton, shizophyllan, picibanil, ubenimex, krestin and the like), antitumor plant components (camptothecin, vindesine, vincristine, vinblastine and the like), BRM (biological response modifier; for example, tumor necrosis factor, indomethacin and the like), cell adhesion inhibitors (for example, substance having RGD sequence, and the like), matrix metalloproteinase inhibitors (for example, marimastat, batimastat and the like), hormones (for example, hydrocortisone, dexamethasone, methylprednisolone, prednisolone, prasterone, betamethasone, triamcinolone, oxymetholone, nandrolone, methenolone, fosfestrol, ethinyl estradiol, chlormadinone, medroxyprogesterone and the like), vitamins (for example, tocopherol and the like), antibiotics (for example, ampicillin, sulbenicillin, cephalexin, cephaloridine, tobramycin, chloramphenicol, tetracycline hydrochloride, kitasamycin, lincomycin hydrochloride and the like) or chemotherapeutic agents (for example, sulfamethizole, sulfamonomethoxine, enoxacin, norfloxacin, ofloxacin, quinoxacin and the like), and the like. Further, an agent containing the segment of a glycosylation-deficient HGF of the present invention can also be used in combination with surgical therapy and radiation therapy. Therefore, a pharmaceutical composition containing the segment of a glycosylation-deficient HGF of the present invention can be used for suppressing invasion, suppressing growth, suppressing metastasis, inducing apoptosis and/or inhibiting neovascularization of tumor, in combination with other anticancer agents and the like and/or surgical therapy or radiation therapy.

When an agent containing the segment of a glycosylation-deficient HGF of the present invention is used as an agent for preventing and treating diseases due to neovascularization, there are exemplified diseases due to neovascularization, such as rheumatic arthritis, psoriasis, Osler-Webber syndrome, myocardial vasculogenesis, telangiectasis, hemophilic arthritis, eye neovascularization diseases (for example, diabetic retinopathy, retinophathy of prematurity, senile macular degeneration, corneal graft rejection, neovascular glaucoma, retrolental fibroplasia, perosis and the like), angiofibroma, benign tumors (for example, angioma, acoustic neuroma, neurofibroma, trachoma, pyogenic granuloma, and the like), hematopoietic organ tumors including leukemia, solid tumors, tumor metastasis, granulation of a wound and the like.

An agent containing the segment of a glycosylation-deficient HGF of the present invention can be widely applied to prevention or treatment of diseases caused by excessive or abnormal stimulation of an endothelial cell. Such diseases are not particularly restricted, and there are specifically exemplified intestinal adhesion, Crohn's disease, atherosclerosis, scleroderma, excess scar formation such as keloid and the like. Further, an agent containing the segment of a glycosylation-deficient HGF of the present invention, particularly, glycosylation-deficient NK4 is useful as a birth control agent based on prevention of neovascularization necessary for embryo implantation, and useful as an agent for preventing or treating diseases associated with neovascularization such as cat scratch disease and ulcer as a pathologic result.

Further, the segment of a glycosylation-deficient HGF can be used as an agent for treatment and prevention of infection diseases such as *Listeria* and malaria.

A base sequence coding the segment of a glycosylation-deficient HGF of the present invention can be used also as a gene pharmaceutical composition. The target diseases in gene therapy include the above-mentioned diseases.

EXAMPLES

The present invention will be further illustrated in detail by the following examples, but the scope of the invention is not limited to these examples.

Abbreviations used in examples are as described below.
HGF: hepatocyte growth factor
bFGF: basic fibroblast growth factor
LB: Luria-Bertani
Amp: ampicillin
SDS-PAGE: SDS-polyacrylamide gel electrophoresis
Tween 80: polyoxyethylene (20) sorbitan monooleate

Example 1

A base sequence coding 5 amino acid-deleted type NK4 shown in SEQ ID NO: 3 was incorporated into a pCAGGS vector. The resulting vector is designated pCAGGS-NK4.

For the purpose of introducing mutations into three glycosylation sites (289th, 397th and 471st of SEQ ID NO: 2) present in the NK4 protein, three mutagenic primers (5'-phosphorylated) shown in Table 1 were synthesized and site-directed mutagenesis was performed using the pCAGGS-NK4 vector as a template. By this mutagenesis, Asn 289th and Asn 397th are substituted by Gln, and Thr 471st is substituted by Gly, among amino acid sequences of the 5 amino acid-deleted type NK4. For the mutagenesis, QuikChange Multi Kit available from STRATAGENE was utilized.

TABLE 1

| Base sequence | Sequence number |
|---|---|
| 5'-tgc gct gac aat act atg caa gac act gat gtt cct ttg-3' | SEQ ID NO: 4 |
| 5'-ggc aaa aat tat atg ggc cag tta tcc caa aca aga tct gg-3' | SEQ ID NO: 5 |
| 5'-tgc aaa cag gtt ctc caa gtt tcc cag ctg gta tat gg-3' | SEQ ID NO: 6 |

The vector containing the introduced mutations was transformed into a competent cell of *E. coli* XL10 Gold, and Amp-resistant colonies were picked up on an LB/Amp plate. Plasmids were extracted from the resulting each clone, and the intended clone was screened by analyzing a base sequence on the coding region of NK4. The vectors having intended three mutations in the base sequence coding NK4 and no other mutation being confirmed were selected and used in the subsequent experiments. The resultant mutated vector is referred to as pCAGGS-NK4-NG.

Next, pCAGGS-NK4-NG was transfected into COS-7 cells. COS-7 cells were cultured in Dulbecco modified Eagle medium (DMEM) supplemented with 10% fetal calf serum (FCS). The medium for the cells was changed to serum-free DMEM just before transfection. Transfection was conducted by a lipofection method using LIPOFECTAMINE 2000 (Invitrogen). At 6 hours after transfection, the medium was changed to DMEM containing 1% FCS and 5 mM benzamidine, and in this procedure, heparin was added to a concentration of 1 μg/mL. After 24 hours, the culture supernatant was collected after filtration through a filter with a pore size of 0.22 μm, then, the medium was changed to a new medium (DMEM containing 1% FCS, 1 μg/mL heparin and 5 mM benzamidine), and culturing was conducted further for 24 hours. After 24 hours, the culture supernatant was again collected in the same manner. The collected supernatant of the culture solution was preserved at −80° C. until purification thereof. The concentration of the glycosylation-deficient NK4 secreted into the culture medium was analyzed by ELISA.

The above-mentioned medium was thawed and mixed, and again filtered through a filter with a pore size of 0.22 μm, then, added at a flow rate of 1 mL/min to HiTrap heparin (Bed volume: 5 mL) (Amersham Bioscience K.K.) equilibrated with 50 mM Tris-hydrochloric acid (pH 7.5), 0.01 Tween 80 and 0.3 M sodium chloride. The column was washed with 50 mM Tris-hydrochloric acid (pH 7.5), 0.01% Tween 80 and 0.3 M sodium chloride, then, the NaCl concentration was raised up to 2 M to elute glycosylation-deficient NK4. Elution was conducted at a flow rate of 1 mL/min, and fractionated at a rate of 2.5 mL/tube. A fraction containing the glycosylation-deficient NK4 was collected, and the buffer was exchanged to 50 mM Tris-hydrochloric acid (pH 7.5), 0.01% Tween 80 and 0.3 M sodium chloride by ultrafiltration. This was added at a flow rate of 0.4 mL/min to a Mini S column (Bed volume: 0.8 mL) (Amersham Bioscience K. K.) equilibrated with the same buffer. The column was washed with 50 mM Tris-hydrochloric acid (pH 7.5), 0.01% Tween 80 and 0.3 M sodium chloride, then, the NaCl concentration was raised up to 1 M to elute glycosylation-deficient NK4. Elution was conducted at a flow rate of 0.4 mL/min, and fractionated at a rate of 0.4 mL/tube. A fraction containing the glycosylation-deficient NK4 was collected, and the purification was confirmed by SDS-PAGE.

An NK4 protein was also prepared using CHO cells according to a method described in JP-A No. 2003-250549 (referred to as glycosylated NK4).

The glycosylated NK4 and glycosylation-deficient NK4 were reduced and allowed to migrate by SDS-PAGE, then, the gel was stained with silver and the results are shown in FIG. 1. The band of the glycosylated NK4 was confirmed at a position corresponding to a molecular weight of 67 kDa. In the glycosylation-deficient NK4, the band shifted to a position (molecular weight of 51 kDa of NK4 protein backbone) corresponding to the molecular weight of sugar chain deficiency.

Example 2

Figure 2:
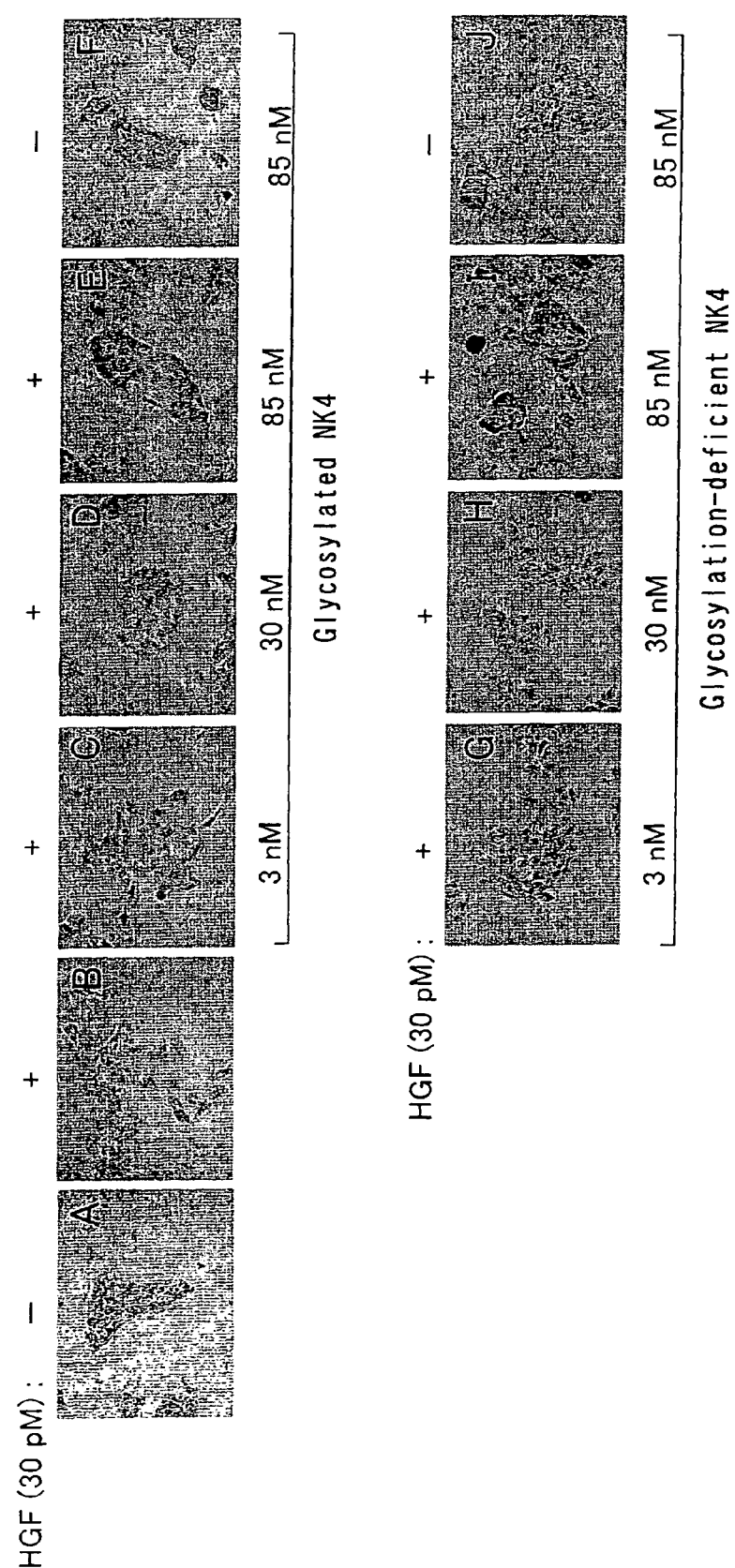
FIG. 2 is a view showing the action of NK4 suppressing cell migration induced by HGF, compared between glycosylated NK4 and glycosylation-deficient NK4.

MDCK-3B cells were suspended in DMEM (containing 10% FCS) and seeded on a 96-well plate to give a density of 5000 cells/well, and HGF was added thereon to provide a concentration of 30 pM. In this procedure, the glycosylated NK4 or glycosylation-deficient NK4 was added simultaneously to provide a concentration of 3 nM, 30 nM or 85 nM, and cultured at 37° C. for 20 hours, then, the extent of scattering was observed by a microscope (FIG. 2). Though the usual morphology of the MDCK-3B cell is as shown in FIG. 2A, when HGF was added and cultured, cells scattered (FIG. 2B). When the glycosylated NK4 was added simultaneously with HGF, scattering of cells was suppressed, and the higher the concentration of the glycosylated NK4 was, the more cell scattering was suppressed (FIGS. 2C, D, E). The glycosylation-deficient NK4 suppressed scattering of the MDCK-3B cell with the same degree as the glycosylated NK4 (FIGS. 2G, H, I). That is, the glycosylation-deficient NK4 showed an HGF antagonist activity of the same degree as the glycosylated NK4. When HGF was not added, the MDCK-3B cell showed no change even if the glycosylated NK4 or glycosylation-deficient NK4 was added (FIGS. 2F, J).

Example 3

Figure 3:
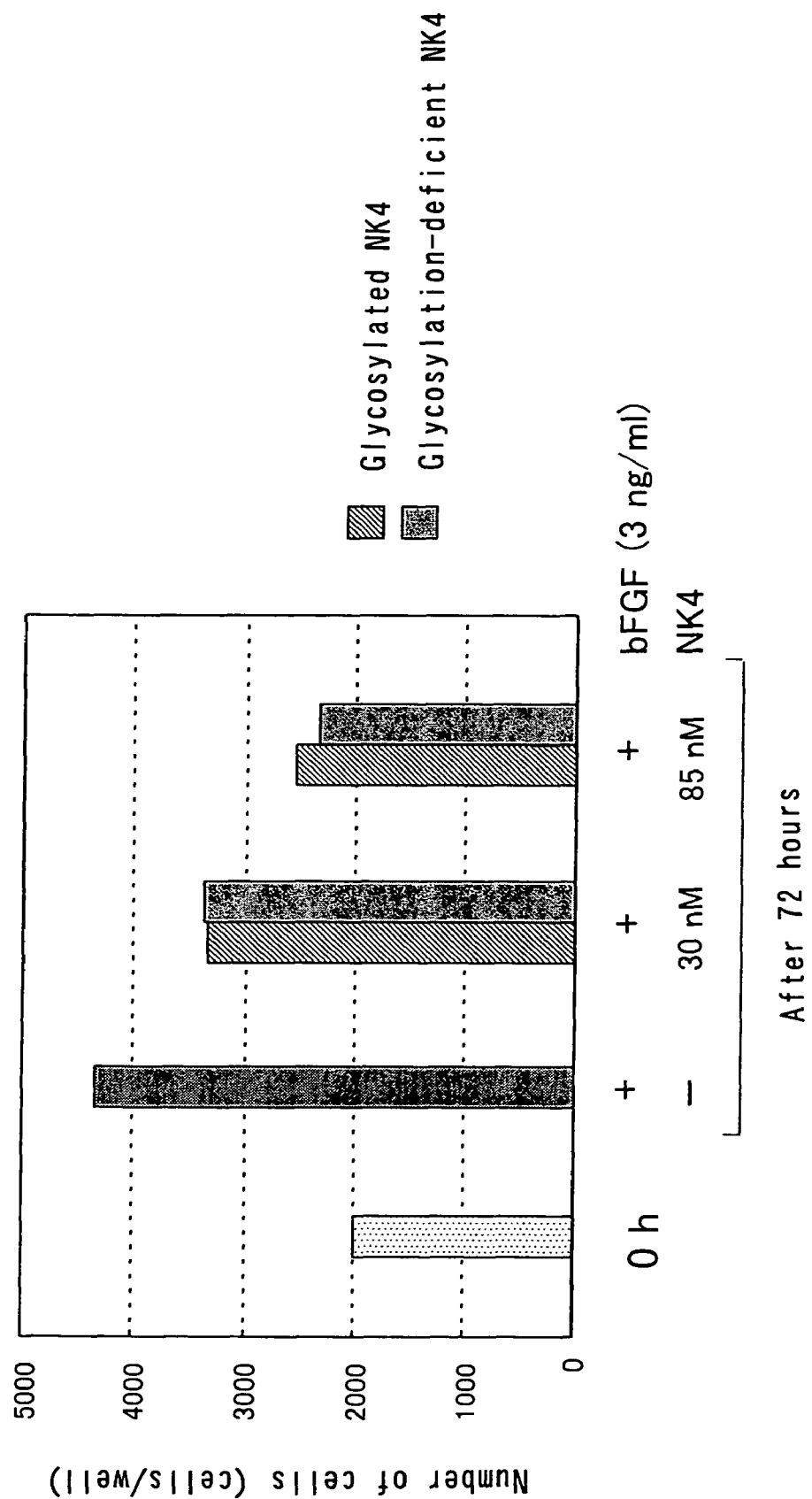
FIG. 3 is a view showing the action of NK4 suppressing_the proliferation of vascular endothelial cells induced by bFGF, compared between glycosylated NK4 and glycosylation-deficient NK4.

Human umbilical vein endothelial cells (HUVEC) were suspended in MDCB131 medium (containing 5% FCS) and seeded on a 96-well plate at a density of 2000 cells/well, and cultured for 24 hours without adding bFGF. Then, the medium was changed to a new MDCB131 medium (containing 5% FCS) and bFGF was simultaneously added to give a concentration of 3 ng/mL, and cultured for 72 hours. In this procedure, the glycosylated NK4 or glycosylation-deficient NK4 was added simultaneously with bFGF to provide a concentration of 30 nM or 85 nM. The number of cells (HUVEC) 72 hours after culturing was counted, and effects of the glycosylated NK4 and glycosylation-deficient NK4 on suppressing proliferation of HUVEC were compared (FIG. 3). When the glycosylated NK4 or glycosylation-deficient NK4 was not added, HUVEC proliferated by the action of bFGF, and the number of cells thereof increased. When the glycosylated NK4 was added simultaneously with bFGF, proliferation of HUVEC was suppressed, and the higher the concentration of the glycosylated NK4 was, the more proliferation of HUVEC was suppressed. The glycosylation-deficient NK4 suppressed proliferation of HUVEC at the same degree as the glycosylated NK4. That is, the glycosylation-deficient NK4 had a neovascularization inhibitory activity of the same degree as the glycosylated NK4.

Example 4

Figure 4:
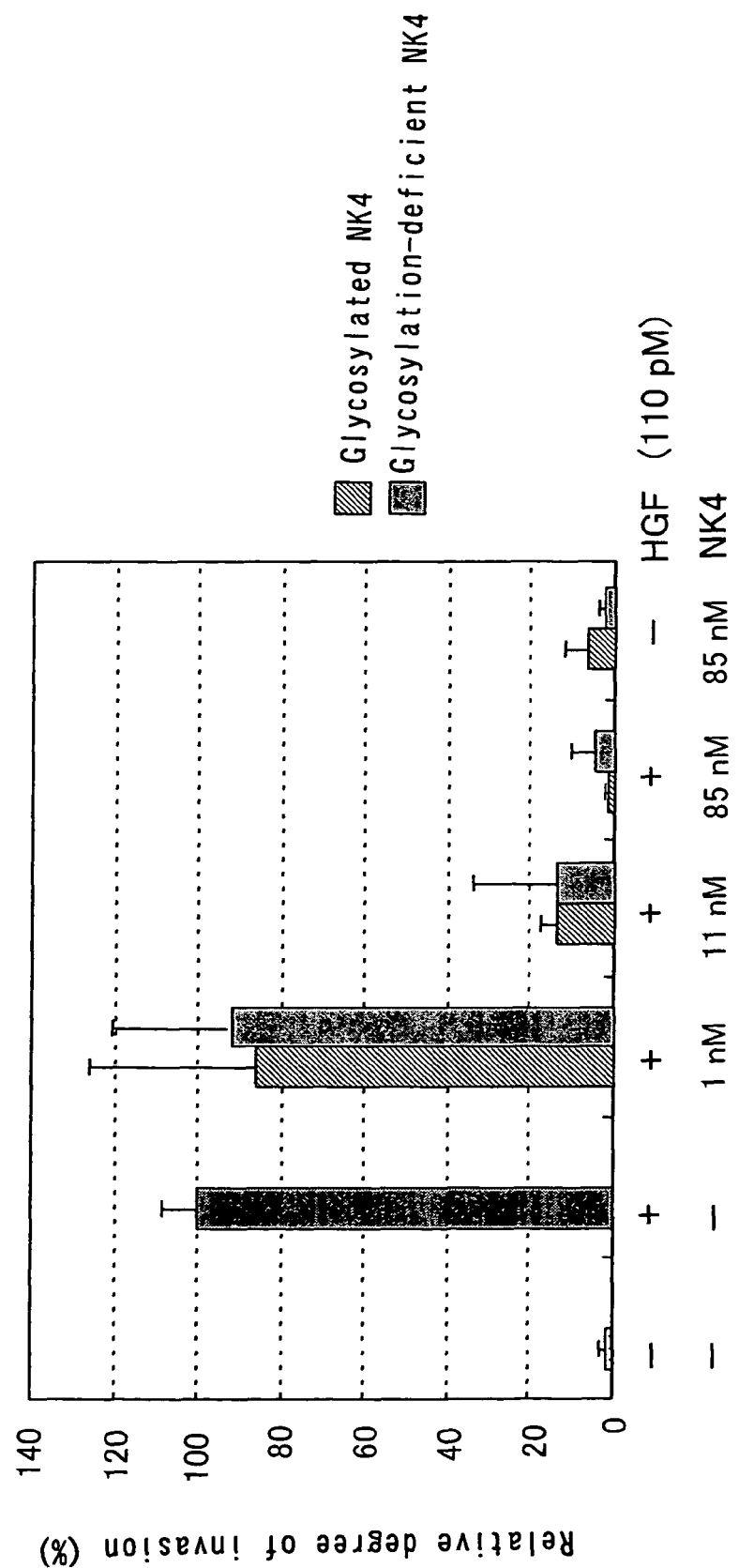
FIG. 4 is a view showing the action of NK4 suppressing the invasion of cancer cells, compared between glycosylated NK4 and glycosylation-deficient NK4.

For examining the action of suppressing invasion of cancer cells by the glycosylated NK4 and glycosylation-deficient NK4, human gallbladder cancer cells (GB-d1) were suspended in DMEM (containing 10% FCS), and added (15000 cells/chamber) into a matrigel chamber (BD BIOCOAT Matrigel chamber, available from BD Biosciences). The chamber was set on a 24-well plate, and DMEM (containing 10% FCS) was added to the outside of the chamber. To the DMEM medium outside the chamber, HGF was added to give a concentration of 110 pM. In this procedure, the glycosylated NK4 or glycosylation-deficient NK4 was added simultaneously to the DMEM medium outside the chamber to provide a concentration of 1 nM, 11 nM or 85 nM and the cells were cultured at 37° C. for 24 hours. Then, the number of GB-d1 cells invaded out of the chamber was counted. The number of invading cells when only HGF was added was defined as 100, and the number of cancer cells invaded out of the chamber was shown as relative value (FIG. 4). The matrigel imitates a basement membrane, and cancer cells in the chamber invade out of the chamber by the action of HGF added outside of the chamber. When the glycosylated NK4 or glycosylation-deficient NK4 was not added, a lot of cancer cells invaded out of the chamber by the invasion-inducing action of HGF. When the glycosylated NK4 was added simultaneously with HGF, invasion of cancer cells was suppressed, and the higher the concentration of the glycosylated NK4 was, the more invasion was suppressed. Further, the glycosylation-deficient NK4 suppressed invasion of the GB-d1 cells at the same degree as the glycosylated NK4.

INDUSTRIAL APPLICABILITY

The segment of a glycosylation-deficient HGF of the present invention is useful as an alternate for a segment of glycosylated HGF.

What is claimed is:

1. An isolated or purified segment of hepatocyte growth factor (HGF) not having any sugar chains at glycosylation sites, (A) wherein said segment is a protein having a homology of at least 80% or higher with amino acids from positions 32 to 478 of SEQ ID NO: 1, (B) wherein said segment,
  (i) lacks sugar chains at glycosylation sites of an HGF α-chain,
  (ii) has an N terminal hairpin domain and four kringle domains,
  (iii) has an antagonist activity against the action of HGF via a c-Met/HGF receptor, and
  (iv) has a neovascularization inhibitory activity, (C) wherein the amino acids of the protein are substituted so as to prevent glycosylation at the glycosylation sites of the protein, and (D) wherein the substitutions of amino acids are the following (a), (b) and (c):

(a) amino acid(s) at position(s) 294 and/or 296 of SEQ ID NO: 1 is/are substituted by another amino acid, and/or an amino acid at position 295 thereof is substituted by Pro, leading thereby to no glycosylation at position 294, (b) amino acid(s) at position(s) 402 and/or 404 of SEQ ID NO: 1 is/are substituted by another amino acid, and/or an amino acid at position 403 thereof is substituted by Pro, leading thereby to no glycosylation at position 402, and (c) an amino acid at position 476 of SEQ ID NO: 1 is substituted by another amino acid, leading thereby to no glycosylation at position 476.

2. The segment of HGF according to claim 1, wherein amino acids at positions 162 to 166 of SEQ ID NO: 1 are deleted.

3. A method of producing the segment of glycosylation-deficient HGF according to claim 1, comprising introducing a vector containing a DNA comprising a base sequence coding the segment of glycosylation-deficient HGF according to claim 1 into a cell, culturing the cell, allowing a segment of glycosylation-deficient HGF to be accumulated in the cell or to be secreted into culture solution of the cell, and collecting and purifying the segment of glycosylation-deficient HGF from the cell or culture solution of the cell.

4. The method of producing the segment of glycosylation-deficient HGF according to claim 3, wherein the cell is a eukaryotic cell.

5. The method of producing the segment of glycosylation-deficient HGF according to claim 4, wherein the eukaryotic cell is a yeast or insect cell.

6. A method of producing the segment of glycosylation-deficient HGF according to claim 1, comprising introducing a vector containing a DNA comprising a base sequence coding the segment of glycosylation-deficient HGF according to claim 1 into an insect individual, allowing a segment of glycosylation-deficient HGF to be accumulated in the insect individual, and collecting and purifying the segment of glycosylation-deficient HGF from the insect individual.

7. An agent comprising as an active ingredient the segment of HGF according to claim 1.

8. The agent according to claim 7, wherein the agent is a neovascularization inhibiting agent.

9. The agent according to claim 7, wherein the agent is an antagonist against the action of HGF mediated via a c-Met/HGF receptor.

10. The agent according to claim 7, wherein the agent is an agent suppressing invasion, growth or metastasis of tumor.

* * * * *

SEQUENCE LISTING

<160> NUMBER OF SEQ ID NOS: 6

<210> SEQ ID NO 1
<211> LENGTH: 494
<212> TYPE: PRT
<213> ORGANISM: Homo Sapiens
<220> FEATURE:
<223> OTHER INFORMATION: alpha-chain of human hepatocyte growth factor

<400> SEQUENCE: 1

Met Trp Val Thr Lys Leu Leu Pro Ala Leu Leu Leu Gln His Val Leu
                 5                  10                  15

Leu His Leu Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
 50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
               100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
               165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
               245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
               325                 330                 335

His Asp Met Thr Pro Glu Asn Phe Lys Cys Lys Asp Leu Arg Glu Asn
            340                 345                 350

```
Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
            405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Ala His
            435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg
            485                 490

<210> SEQ ID NO 2
<211> LENGTH: 489
<212> TYPE: PRT
<213> ORGANISM: Homo Sapiens
<220> FEATURE:
<223> OTHER INFORMATION: alpha-chain of human hepatocyte growth factor
      of five amino acid-deleted type

<400> SEQUENCE: 2

Met Trp Val Thr Lys Leu Leu Pro Ala Leu Leu Leu Gln His Val Leu
                5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220
```

| | | | | | | | | | | | |
|---|---|---|---|---|---|---|---|---|---|---|---|
|Lys|Ile|Cys|Gln|Arg|Trp|Asp|His|Gln|Thr|Pro|His|Arg|His|Lys|Phe|
|225| | | |230| | | |235| | | |  | |240| |

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
    290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
            325                 330                 335

Glu Asn Phe Lys Cys Lys Asp Leu Arg Glu Asn Tyr Cys Arg Asn Pro
        340                 345                 350

Asp Gly Ser Glu Ser Pro Trp Cys Phe Thr Thr Asp Pro Asn Ile Arg
    355                 360                 365

Val Gly Tyr Cys Ser Gln Ile Pro Asn Cys Asp Met Ser His Gly Gln
370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
            405                 410                 415

Leu His Arg His Ile Phe Trp Glu Pro Asp Ala Ser Lys Leu Asn Glu
        420                 425                 430

Asn Tyr Cys Arg Asn Pro Asp Asp Ala His Gly Pro Trp Cys Tyr
    435                 440                 445

Thr Gly Asn Pro Leu Ile Pro Trp Asp Tyr Cys Pro Ile Ser Arg Cys
    450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg
            485

<210> SEQ ID NO 3
<211> LENGTH: 1422
<212> TYPE: DNA
<213> ORGANISM: Homo Sapiens
<220> FEATURE:
<223> OTHER INFORMATION: NK4 of five amino acid-deleted type

<400> SEQUENCE: 3

```
atgtgggtga ccaaactcct gccagccctg ctgctgcagc atgtcctcct gcatctcctc    60
ctgctcccca tcgccatccc ctatgcagag ggacaaagga aagaagaaa  tacaattcat   120 gaattcaaaa aatcagcaaa gactacccta atcaaaatag atccagcact gaagataaaa   180
accaaaaaag tgaatactgc agaccaatgt gctaatagat gtactaggaa taaggactt    240 ccattcactt gcaaggcttt tgtttttgat aaagcaagaa acaatgcct  ctggttcccc   300 ttcaatagca tgtcaagtgg agtgaaaaaa gaatttggcc atgaatttga cctctatgaa   360
aacaaagact acattagaaa ctgcatcatt ggtaaaggac gcagctacaa gggaacagta   420
tctatcacta gagtggcat  caaatgtcag ccctggagtt ccatgatacc acacgaacac   480
agctatcggg gtaaagacct acaggaaaac tactgtcgaa atcctcgagg ggaagaaggg   540
```

-continued

```
ggaccctggt gtttcacaag caatccagag gtacgctacg aagtctgtga cattcctcag    600
tgttcagaag ttgaatgcat gacctgcaat ggggagagtt atcgaggtct catggatcat    660
acagaatcag gcaagatttg tcagcgctgg gatcatcaga caccacaccg gcacaaattc    720
ttgcctgaaa gatatcccga caagggcttt gatgataatt attgccgcaa tcccgatggc    780
cagccgaggc catggtgcta tactcttgac cctcacaccc gctggagta ctgtgcaatt     840 aaaacatgcg ctgacaatac tatgaatgac actgatgttc ctttggaaac aactgaatgc    900
atccaaggtc aaggagaagg ctacaggggc actgtcaata ccatttggaa tggaattcca    960
tgtcagcgtt gggattctca gtatcctcac gagcatgaca tgactcctga aaatttcaag   1020
tgcaaggacc tacgagaaaa ttactgccga aatccagatg ggtctgaatc accctggtgt   1080
tttaccactg atccaaacat ccgagttggc tactgctccc aaattccaaa ctgtgatatg   1140
tcacatggac aagattgtta tcgtgggaat ggcaaaaatt atatgggcaa cttatcccaa   1200
acaagatctg gactaacatg ttcaatgtgg gacaagaaca tggaagactt acatcgtcat   1260
atcttctggg aaccagatgc aagtaagctg aatgagaatt actgccgaaa tccagatgat   1320
gatgctcatg gacctggtg ctacacggga aatccactca ttccttggga ttattgccct    1380
atttctcgtt gtgaaggtga taccacacct acaatagtct ga                      1422
```

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: synthetic construct

<400> SEQUENCE: 4
tgcgctgaca atactatgca agacactgat gttcctttg                          39

<210> SEQ ID NO 5
<211> LENGTH: 41
<212> TYPE: DNA
<213> ORGANISM: Artificial Sequence
<220> FEATURE:
<223> OTHER INFORMATION: Description of Artificial Sequence: synthetic construct

<400> SEQUENCE: 5
ggcaaaaatt atatgggcca gttatcccaa acaagatctg g                       41

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: synthetic construct

<400> SEQUENCE: 6
tgcaaacagg ttctccaagt ttcccagctg gtatatgg                           38